US008957186B2

(12) United States Patent
Ahn et al.

(10) Patent No.: US 8,957,186 B2
(45) Date of Patent: Feb. 17, 2015

(54) RECOMBINANT PROTEIN FOR INTRACELLULAR DELIVERY OF SIRNA AND COMPOSITION COMPRISING THE SAME

(75) Inventors: Hyung-Jun Ahn, Seoul (KR); Ick-Chan Kwon, Seoul (KR); Kui-Won Choi, Seoul (KE)

(73) Assignee: Korea Institute of Science and Technology, Seoul (KR)

( * ) Notice: Subject to any disclaimer, the term of this patent is extended or adjusted under 35 U.S.C. 154(b) by 357 days.

(21) Appl. No.: 13/313,580

(22) Filed: Dec. 7, 2011

(65) Prior Publication Data

US 2013/0150287 A1    Jun. 13, 2013

(30) Foreign Application Priority Data

May 11, 2010    (KR) ........................ 10-2011-0043727

(51) Int. Cl.
*A61K 47/48* (2006.01)
*C07H 21/04* (2006.01)
(52) U.S. Cl.
USPC ......... 530/350; 530/300; 514/44 R; 536/23.1; 536/24.5; 435/4; 435/91.1; 435/91.31; 435/455
(58) Field of Classification Search
USPC ........... 530/300, 350; 514/44; 536/23.1, 24.5; 435/6, 91.1, 91.31, 455
See application file for complete search history.

(56) References Cited

U.S. PATENT DOCUMENTS 7,018,826 B1 *   3/2006   Hildt et al. ................. 435/235.1
7,144,712 B2 *  12/2006   Milich et al. ................. 435/69.3

FOREIGN PATENT DOCUMENTS

WO    WO 2009/058814    *   5/2009    ............ G01N 33/53

OTHER PUBLICATIONS

Hatton et al., 1992, RNA-and DNA-Binding Activities in Hepatitis B Virus Capsid Protein: a Model for Their Roles in Viral Replication, Journal of Virology, 66(9): 5232-5241.*
Sun et al., 2002, Anti-HBV effects of genetically engineered replication-defective HBV with combined expression of antisense RNA and dominant negative mutants of core protein and construction of first-generation packaging cell line for HBV vector, Chin J Hepatol, 10(4): 260-265.*
Pumpens et al., 2001, HBV Core Particles as a Carrier for B Cell/T Cell Epitopes, Intervirology, 44: 98-114.*
Chambers et al., 1996, Chimeric Hepatitis B Virus Core Particles as Probes for Studying Peptide-Integrin Interactions, Journal of Virology, 70(6): 4045-4052.*
Porterfield et al., 2010, Full-Length Hepatitis B Virus Core Protein Packages Viral and Heterologous RNA with Similarly High Levels of Cooperativity, Journal of Virology, 84(14): 7174-7184.*

(Continued)

*Primary Examiner* — Amber D Steele
(74) *Attorney, Agent, or Firm* — Staas & Halsey LLP

(57) ABSTRACT

The present invention relates to a recombinant protein for siRNA delivery, which allows the efficient intracellular and in vivo delivery of siRNA. More particularly, the present invention relates to a recombinant protein that allows a siRNA binding protein to be located in the interior cavity of a capsid protein of HBV (Hepatitis B virus), in which siRNAs of interest bind to the siRNA binding protein to be encapsulated within the capsid shell, thereby providing stability against the external attack such as nucleases and achieving the efficient intracellular and in vivo delivery of siRNA by its release into the cytosolic space after cell uptake.

10 Claims, 10 Drawing Sheets

(56) References Cited

OTHER PUBLICATIONS

Vogel et al., 2005, Quaternary Structure is Critical for Protein Display on Capsid-Like Particles (CLPs): Efficient Generation of Hepatitis B Virus CLPs Presenting Monomeric but not Dimeric and Tetrameric Fluorescent Proteins, 2005, Proteins: Structure, Function, and Bioinformatics, 58: 478-488.*

Kratz et al., 1999, Native display of complete foreign protein domains on the surface of hepatitis B virus capsids, PNAS, 96: 1915-1920.*

Choi et al., published online Oct. 10, 2011, Chimeric Capsid Protein as a Nanocarrier for siRNA Delivery: Stability and Cellular Uptake of Encapsulated siRNA, ACSNano, 5(11): 8690-8699.*

Shlomai et al., 2009, The "Trojan Horse" model-delivery of anti-HBV small interfering RNAs by a recombinant HBV vector, Biochemical and Biophysical Research Communications, 390: 619-623.*

Irena Melnikova, "RNA-based Therapies," *Nature Review Drug Discovery,* vol. 6, pp. 863-864., Nov. 2007.

Yu-Kyoung Oh et al., "siRNA Delivery Systems for Cancer Treatment," *Advanced Drug Delivery Review,* vol. 61, pp. 850-862, 2009.

Young Hun Choi, et al., "Polyethylene Glycol-grafted Poly-L-lysine as Polymeric Gene Carrier," *Journal of Controlled Release,* vol. 54, 39-48. 1998.

Arik Cooper et al. "Recombinant viral capsids as an efficient vehicle of oligonucleotide delivery into cells", Biochemical and Biophysical Research Communication, vol. 327, pp. 1094-1099, Feb. 2005.

* cited by examiner

FIG. 1

SEQ ID NO: 5

```
        10        20        30        40        50        60
         |         |         |         |         |         |
MDIDPYKEFGATVELLSFLPSDFFPSVRDLLDTASALYREALESPEHCSPHHTALRQAIL
        70        80        90       100       110       120
         |         |         |         |         |         |
CWGELMTLATWVGNNLEDPCDCRGDCFCRDLVVNYVNTNMGLKIRQLLWFHISCLTFGRE
       130       140       150       160       170       180
         |         |         |         |         |         |
TVLEYLVSFGVWIRTPPAYRPPNAPILSTLPETTVVGSSGGSGSSGGSGGGDEADGSRGS
       190       200       210       220       230       240
         |         |         |         |         |         |
QKAGVDERAIQGNDTREQANGERWDGGSGGITSPFKLPDESPSWTEWRLYNDETNSNQDN
       250       260       270       280       290       300
         |         |         |         |         |         |
PLGFKESWGFGKVVFKRYLRYDRTEASLHRVLGSWTGDSVNYAASRFLGANQVGCTYSIR
       310       320       330       340       350
         |         |         |         |         |
FRGVSVTISGGSRTLQHLCEMAIRSKQELLQLTPVEVESNVSRGCPEGIETFKKESE
```

FIG. 5
FIG. 6
(A) 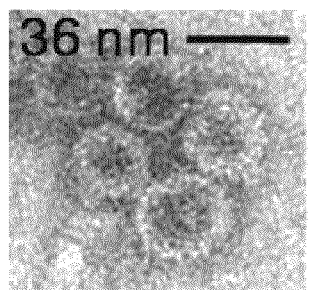   (B) 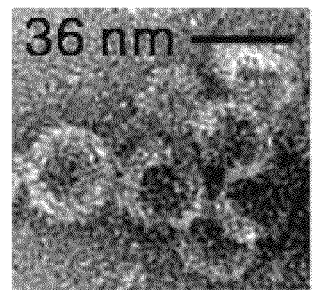

FIG. 10
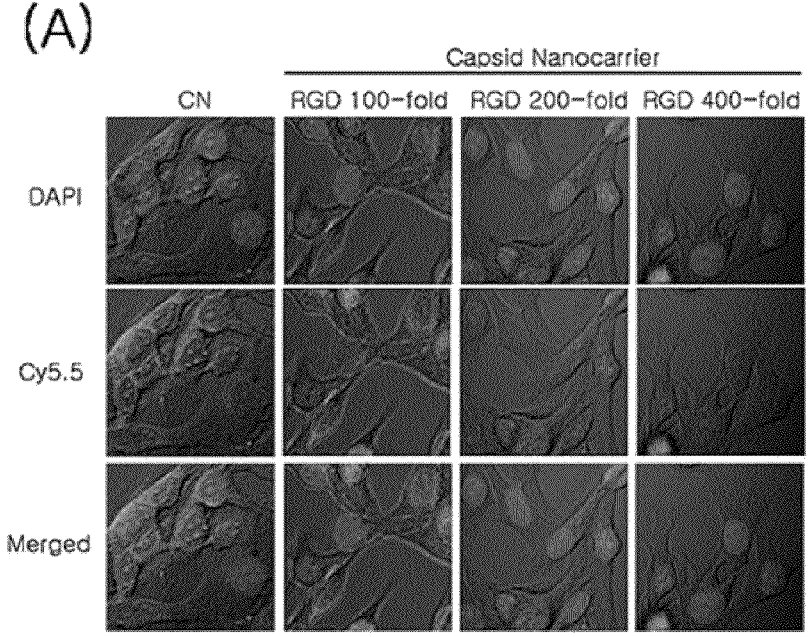
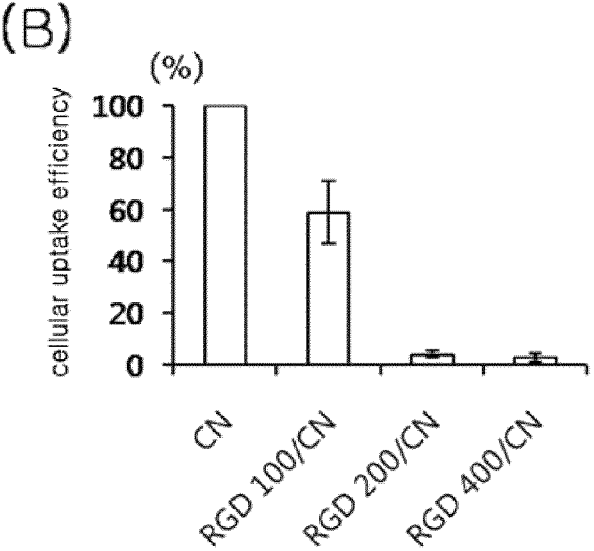

FIG. 13
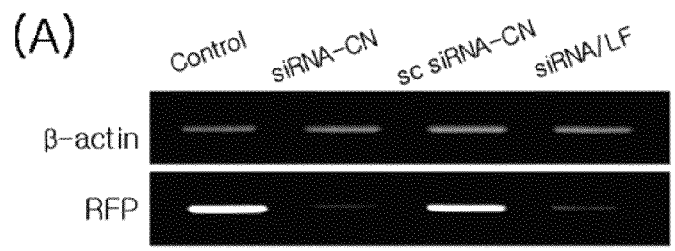
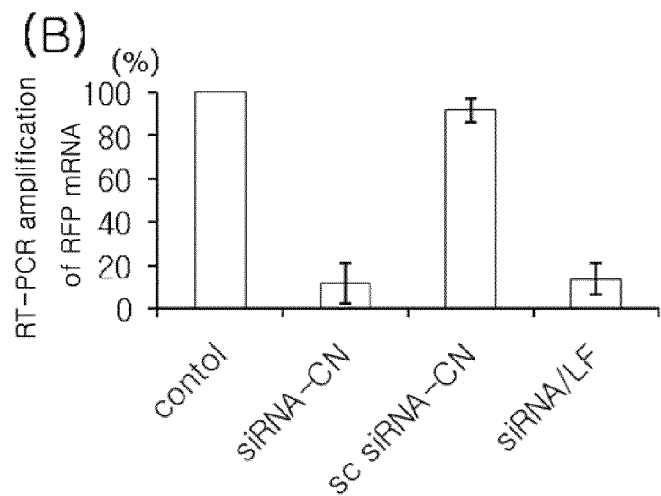
FIG. 14
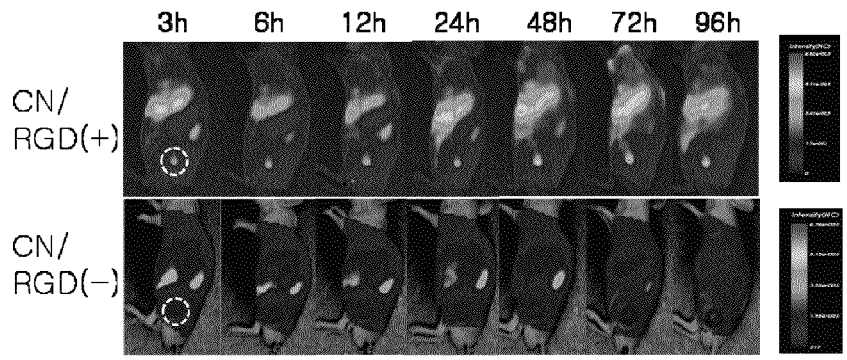

Immunohistochemistry

RECOMBINANT PROTEIN FOR INTRACELLULAR DELIVERY OF SIRNA AND COMPOSITION COMPRISING THE SAME

CROSS REFERENCE TO RELATED APPLICATIONS

This application claims the benefit of Korean Application No. 10-2011-0043727, filed May 11, 2011, the disclosure of which is incorporated herein by reference.

BACKGROUND OF THE INVENTION

1. Field of the Invention

The present invention relates to a recombinant protein for siRNA delivery, which allows the efficient intracellular and in vivo delivery of siRNA. More particularly, the present invention relates to a recombinant protein comprising (1) a capsid protein of HBV (Hepatitis B virus) and (2) a siRNA binding protein that is located in the interior cavity of the recombinant protein. In the recombinant protein, siRNAs of interest bind to the siRNA binding protein to be encapsulated within the recombinant protein particle, thereby providing stability against the external attack such as nucleases and achieving the efficient intracellular and in vivo delivery of siRNA by its release into the cytosolic space after cell uptake. Also, RGD peptides are introduced on the exterior surface of the recombinant protein, thereby effectively targeting cancer cells and tissues and achieving silencing of the target gene.

2. Description of the Related Art

RNAi (RNA interference) refers to a phenomenon of selectively inducing degradation of targeted mRNAs or suppressing target gene expression by intracellular introduction of a double stranded RNA consisting of a sense RNA homologous to mRNA of a target gene and an antisense RNA having a sequence complementary to the sense RNA. First discovered in nematodes, RNAi is a highly conserved biological process among animals and plants, such as yeasts, insects, plants and humans.

An RNAi-inducing entity, siRNA (small interference RNA) is a short, double-stranded RNA consisting of approximately 20 to nucleotides. Intracellular delivery of siRNA can suppress expression of a targeted mRNA having complementary base sequence to the siRNA. Thus, siRNA has been regarded as a revolutionary tool for manipulating target biological processes owing to its therapeutic effects on diseases, easy preparation and high target selectivity.

Currently, cancer, viral infections, autoimmune diseases and neurodegenerative diseases have been explored as promising disease targets of siRNAs. Clinical studies have demonstrated the potential of siRNAs as a therapeutic agent for age-related macular degeneration (bevasiranib; Opko Health, Inc., Miami, Fla., USA; phase III), and respiratory syncytial virus infection (ALN-RSV01; Alnylam, Cambridge, Mass., USA; phase II) (Melnikova I. Nat Rev Drug Discov 2007, 6, 863-864). Moreover, human cancer therapy via systemic delivery of siRNA using transferrin-tagged, cyclodextrin-based polymeric nanoparticles (CALAA-01; Calando Pharmaceuticals, Pasadena, Calif., USA; phase I) has been recently announced (Oh Y K. et al., Adv Drug Deliver Rev 2009, 61, 850-862).

However, siRNA has low stability and is quickly degraded in vivo, and the anionic nature of siRNA hinders it from permeating a cell membrane with negative charge, leading to low levels of siRNA transfer into intracellular compartments. Accordingly, there is a need to develop a technology for the preparation of an effective delivery system that facilitates intracellular transfer of siRNA. Thus, novel delivery systems, which enable prolonged circulation of siRNA with resistance against enzymatic degradation, high accessibility to target cells via clinically feasible administration routes, and optimized cytosolic release of siRNA after efficient cellular uptake, are indispensably required for the efficient intracellular delivery of siRNAs.

As a siRNA delivery system, a siRNA-expressing recombinant plasmid or viral vector has been generally used. Alternatively, lipofectin, lipofectamine, cellfectin, cationic phospholipid nanoparticle, polycation, or liposome-based systems have been mainly used. However, the viral delivery system is problematic in that it is limited by the size of gene to be introduced, and generates side effects induced by immunogenic surface proteins of the viral vector to cause safety problems. There are also drawbacks in that the delivery systems using such cationic molecules or synthetic polymers have lower transfection efficiency and might induce cytotoxicity during intracellular gene delivery.

Therefore, the present inventors have made an effort to develop a novel siRNA delivery carrier showing enhanced stability and cellular uptake by improving the problems of the known siRNA delivery carriers. As a result, the present inventors designed a recombinant protein delivery carrier, in which siRNA is encapsulated within a spherical virus capsid protein to be protected from the external nucleases, leading to the enhanced stability, and siRNA can be delivered into the cytosol of the target cells by facilitating endosomal escape. Further, RGD peptides, which specifically bind with cancer cells to facilitate cellular uptake, are introduced on the exterior surface of the recombinant protein delivery carrier, thereby providing cancer targeting capability. Furthermore, the present inventors demonstrated the excellent potential of the recombinant protein as a delivery carrier via tests on its siRNA affinity, cellular uptake efficiency, in vivo stability and cancer targeting capability, thereby completing the present invention.

SUMMARY OF THE INVENTION

An object of the present invention is to provide a recombinant protein for siRNA delivery, comprising a capsid protein of HBV (Hepatitis B virus) and a siRNA binding protein that is located in the interior cavity of the recombinant protein.

Preferably, an object of the present invention is to provide a recombinant protein for siRNA delivery, in which a target-specific peptides such as RGD (Arg-Gly-Asp) peptides are bound on the surface of the recombinant protein.

Another object of the present invention is to provide a composition for siRNA delivery comprising the recombinant protein and siRNA, in which the siRNA binds to a siRNA binding protein to be located in the interior cavity of the recombinant protein.

Preferably, another object of the present invention is to provide a composition for siRNA delivery, in which RGD (Arg-Gly-Asp) peptides are bound on the surface of the recombinant protein, and thus allow siRNA to be delivered to cancer tissue.

Still another object of the present invention is to provide a composition for the treatment of diseases associated with siRNA comprising the recombinant protein and siRNA, in which the siRNA binds to a siRNA binding protein to be located in the interior cavity of the recombinant protein.

Preferably, still another object of the present invention is to provide a composition for the treatment of cancer, comprising RGD (Arg-Gly-Asp) peptides bound on the exterior surface of the recombinant protein.

Still another object of the present invention is to provide a method for delivering siRNA, comprising the step of administering the recombinant protein and siRNA to a subject.

Still another object of the present invention is to provide a method for treating diseases associated with siRNA, comprising the step of administering the recombinant protein and siRNA to a subject.

BRIEF DESCRIPTION OF THE DRAWINGS

FIG. 1 shows the amino acid sequence of a subunit that is included in a recombinant protein for siRNA delivery prepared in Example 1 of the present invention, in which each amino acid sequence of a capsid protein of HBV virus (dotted box), a RGD peptide (red box), a linker peptide linking the capsid protein and p19 protein (blue underline), and a p19 protein (dashed box) is indicated;

FIG. 5 is the result of electrophoresis showing determination of the quantitative molar ratio between the siRNA and the recombinant protein particle of the present invention (CN: recombinant protein particle, siRNA+CN: injection of siRNA to recombinant protein particle);

FIG. 6 (A) is the results of electron microscopy showing the recombinant protein particle of the present invention with a diameter of approximately 36 nm, and (B) is the results of electron microscopy showing the siRNA-encapsulated recombinant protein particle;

FIG. 10 is the results of fluorescence microscopy (A) and quantitative analysis (B) showing that the RGD peptides exposed on the recombinant protein particle allow the recombinant protein particle to be recognized by the cancer cell and be subsequently internalized via endocytosis (CN: treatment with recombinant protein particle of the present invention, RGD100-fold or RGD100/CN: treatment with recombinant protein particle after pretreatment with 100-fold of RGD peptide, RGD200-fold or RGD200/CN: treatment with recombinant protein particle after pretreatment with 200-fold of RGD peptide, RGD300-fold or RGD300/CN: treatment with recombinant protein particle after pretreatment with 300-fold of RGD peptide);

FIG. 13 is the results of electrophoresis (A) and quantitative RT-PCR analysis (B) showing degradation of the RFP mRNA by siRNA in FIG. 11 (Control: RFG-expressing B16F10 cell, siRNA-CN: injection of siRNAs into cells using the recombinant protein particle, sc siRNA-CN: injection of mismatched scrambled RFP siRNA encapsulated in the recombinant protein particle into cells, siRNA/LF: use of the known siRNA delivery carrier, Lipofectamine);

FIG. 14 is the results of fluorescence analysis showing that the recombinant protein particles are accumulated in the cancer tissues of animal cancer models by the RGD peptides exposed on the recombinant protein particle, in which CN/RGD(+) represents injection of the recombinant protein particles having RGD peptides on their surface; and CN/RGD(−) represents injection of the recombinant protein particles having no RGD peptides on their surface;

DETAILED DESCRIPTION OF THE PREFERRED EMBODIMENTS

Figure 2:
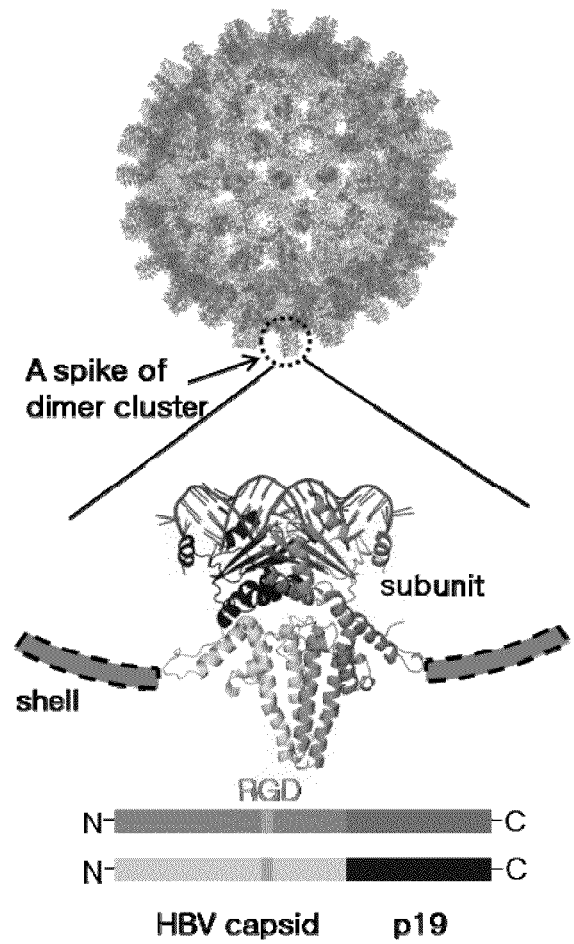
FIG. 2 shows a three-dimensional structure of a recombinant protein particle of the present invention, which is composed of the subunits comprising capsid subunit protein, the RGD peptide, and the p19 protein.
Figure 3:
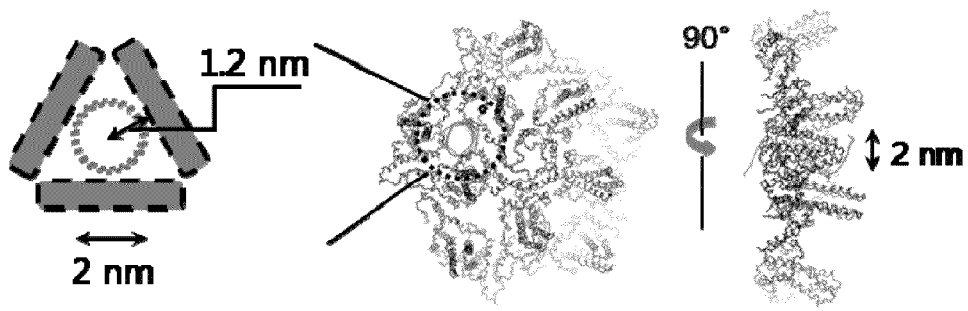
FIG. 3 is the result of simulation showing that siRNA molecules could freely pass through the holes present on the surface of the recombinant protein particle of the present invention.

In one embodiment to achieve the above objects, the present invention relates to a recombinant protein for siRNA delivery, comprising a capsid protein of HBV (Hepatitis B virus) and a siRNA binding protein.

The recombinant protein for siRNA delivery is characterized in that the siRNA binding protein is located within a spherical virus particle formed by the HBV capsid protein, resulting in encapsulation of siRNA within the virus particle.

As used herein, the term "HBV capsid protein" refers to a protein that forms a spherical virus particle via self-assembly when expressed in bacteria such as *E. coli*. The natural HBV capsid protein is a protein that forms a shell in HBV, and a capsid protein forms a virus particle consisting of 240 subunits. The dimer clustering of two subunits produces spikes on the surface of the particle, and there are 120 spikes on one virus particle. The spherical virus particle is known to have an overall diameter of approximately 36 nm.

As used herein, the term "recombinant virus particle" or "recombinant protein particle" refers to a carrier capable of delivering siRNA into the cell, which is formed by self-assembly of the capsid protein, and it may be a nanoparticle having an average diameter of 30 to 500 nm, preferably 30 to 100 nm, but is not limited thereto.

As used herein, the term "recombinant protein for siRNA delivery" means a recombinant protein particle that is composed of a subunit containing a complex of the HBV capsid protein and the siRNA binding protein, in which the siRNA binding protein binding to the HBV capsid protein is located within the particle when the HBV capsid protein forms a spherical recombinant virus particle via self-assembly.

Also, the term "recombinant protein for siRNA delivery", as used herein, is interchangeable with "recombinant virus particle" or "recombinant protein particle".

In the present invention, the HBV capsid protein is advantageous in that its surface is modified with various target-specific peptides using a genetic recombinant method, thereby achieving targeted siRNA delivery, and siRNA is encapsulated in the interior cavity of the spherical virus particle formed by the capsid protein to be protected from the external attack, thereby enhancing in vivo stability of siRNA. Thus, the HBV capsid protein can be effectively used as a siRNA delivery carrier.

Preferably, the HBV capsid protein of the present invention may include a subunit protein having an amino acid sequence of GenBank Accession No. CAA26537.1 or SEQ ID NO. 1. The variants resulting from substitution, insertion, or deletion in the above sequence are also included in the scope of the present invention, as long as they may form spherical virus particles. The capsid protein of the present invention forms a spherical particle via self-assembly, which contains 240 subunit proteins and has an overall diameter of several tens nm.

For example, the HBV capsid protein of the present invention may include a subunit protein having the truncated C-terminus in the amino acid sequence of SEQ ID NO. 1, and preferably a subunit protein having the amino acid sequence at 1 to 149 positions of SEQ ID NO. 1. Further, the HBV capsid protein of the present invention may include a subunit protein having a target-specific peptide, preferably a subunit protein having a target-specific peptide insertion in the amino acid sequence of SEQ ID NO. 1, and more preferably a subunit protein having an RGD peptide insertion between the positions 79 (Pro) and 89 (Arg) of the amino acid sequence. For example, a protein having an RGD peptide insertion between the positions 80 and 81 of the amino acid sequence may be used, but is not limited thereto.

As such, various target-specific peptides bound on the surface of the recombinant protein of the present invention are able to enhance target-specific delivery. As used herein, the term "target-specific peptide" refers to a peptide that is introduced on the surface of the siRNA recombinant protein of the present invention to direct the targeted siRNA delivery. Preferably, the target-specific peptide is, inserted in the amino acid sequence constituting the HBV capsid protein, located on the exterior surface of the spherical virus particle during particle formation by self-assembly, so as to direct the delivery to the target cells.

Preferably, the target-specific peptide may include an RGD (Arg-Gly-Asp) peptide. The RGD peptide is exposed on the exterior surface of the virus particle and thus binds to integrin overexpressed on cancer cells, thereby achieving efficient targeting of the cancer cells. The RGD peptide may be preferably those consisting of 3 to 30 amino acid residues, for example, a RGD peptide of SEQ ID NO. 3 (CDCRGDCFC), but is not limited thereto.

As used herein, the term "siRNA binding protein" refers to a protein that binds with siRNA and sequesters it within the particle, and preferably a CIRV (Carnation Italian ringspot virus)-derived p19 protein, but is not limited thereto. The p19 protein is able to bind with double-stranded RNAs in the size range of 20 to 23 nucleotides with high affinity, but does not bind with single-stranded RNAs, double-stranded DNAs, and ribosomal RNAs, thereby being suitably used as the siRNA binding protein of the present invention.

The siRNA binding protein is fused at the C-terminus of the capsid protein and thus located in the interior cavity of the recombinant virus particle, resulting in encapsulation of siRNA within the particle. Thus, siRNA can be protected from the external attack such as nucleases. In one specific embodiment, the siRNA binding protein of the present invention may be a p19 protein having an amino acid sequence of GenBank CAA59481.1 or SEQ ID NO. 2, and preferably a protein having the amino acid sequence at 3 to 172 positions of SEQ ID NO. 2.

In the present invention, the HBV capsid protein and the siRNA binding protein may be linked with each other via a linker peptide. As used herein, the term "linker peptide" is a peptide that links the HBV capsid protein with the siRNA binding protein, and refers to a peptide that allows the siRNA binding protein to be located within the recombinant virus particle while it does not hinder self-assembly of the capsid protein and dimerization of siRNA binding protein. Any amino acid sequence may be used, as long as the peptide has the above functions. Preferably, the linker peptide has a length sufficient to form a spherical recombinant particle even after fusion of the p19 protein with the capsid protein. More preferably, it may be a peptide consisting of 31 to 300 amino acids. In one preferred embodiment, the linker peptide may be a peptide (GSSGGSGSSGGSGGGDEADGSRG-SQKAGVDE) consisting of 31 amino acids, represented by SEQ ID NO. 4, but is not limited thereto.

In one preferred embodiment, the recombinant protein for siRNA delivery of the present invention is a recombinant protein including a subunit of the following structure:

A-B-C wherein A is a subunit protein of a HBV capsid having a target-specific peptide on its surface;
B is a linker peptide; and
C is a siRNA binding protein bound within the HBV capsid protein.

In another embodiment, the recombinant protein for siRNA delivery of the present invention is a recombinant protein including a subunit of the following structure:

A-B-C wherein A is a subunit protein of a HBV capsid having RGD (Arg-Gly-Asp) on its surface;

B is a linker peptide; and

C is a p19 protein bound within the HBV capsid protein.

In still another embodiment, the recombinant protein for siRNA delivery of the present invention is a recombinant protein including a subunit of the following structure:

A-B-C wherein A is a subunit protein of a HBV capsid, which has the amino acid sequence at 1 to 149 positions of SEQ ID NO. 1 and has an RGD peptide insertion between the amino acid positions 80 and 81;

B is a linker peptide having an amino acid sequence of SEQ ID NO. 4; and

C is a p19 protein, which has the amino acid sequence at 3 to 172 positions of SEQ ID NO. 2 and is bound within the HBV capsid protein.

Preferably, the recombinant protein having the structure of A-B-C may be represented by an amino acid sequence of SEQ ID NO. 5, in which each amino acid sequence included in the entire sequence is shown in FIG. 1.

In a specific Example of the present invention, as shown in FIG. 1, a recombinant protein was designed by linking the HBV capsid subunit protein, which has the amino acid sequence at 1 to 149 positions of SEQ ID NO. 1 and an insertion of the RGD peptide of SEQ ID NO. 4 between the amino acid positions 80 and 81, with the p19 protein having the amino acid sequence at 3 to 172 positions of SEQ ID NO. 2 via the linker of SEQ ID NO. 4, and the 3D structural simulation showed that siRNA molecules could pass through the holes and reach the interior of the designed recombinant protein. Practically, the designed recombinant protein particle was prepared (see Example 1).

Figure 4:
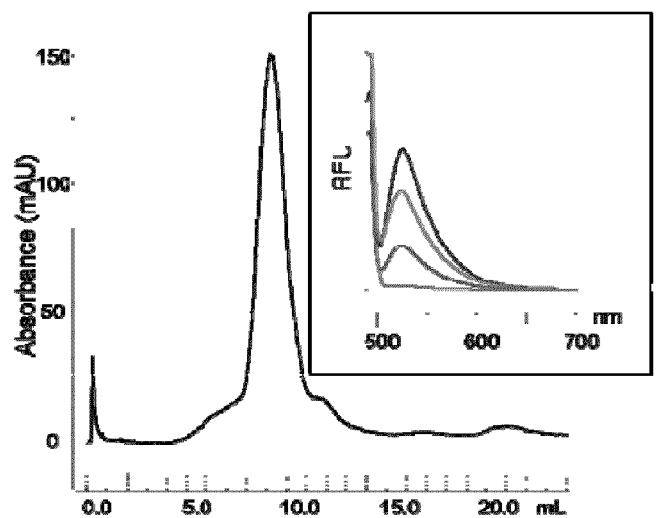
FIG. 4 shows the result of size exclusion chromatography (SEC) and the result of analyzing the peak fractions of the SEC profile using a fluorescence spectrophotometer (in box) in order to examine whether siRNAs are encapsulated within the recombinant protein particle of the present invention.

The present inventors performed size exclusion chromatography and fluorescence analysis, and demonstrated that the prepared recombinant protein formed a spherical particle by self-assembly and the particle can encapsulate siRNA inside the particle (see FIG. 4). They also performed quantitative analysis, and demonstrated that a single recombinant protein particle is able to encapsulate 120 RNA molecules (see FIG. 5). Further, the electron microscopy analysis showed that the recombinant protein prepared according to the present invention formed a spherical nanoparticle with a diameter of approximately 36 nm, similar to HBV (see FIG. 6).

The MTT results showed that the recombinant protein of the present invention had a biocompatibility up to 1 μM (see FIG. 7), and siRNA were dissociated from the recombinant protein under the acidic condition, thereby facilitating the cytosolic release of siRNA by endosomal escape (see FIG. 8). Stability against the external attack such as ribonucleases was maintained by the encapsulation of siRNA in the particle formed by the recombinant protein (see FIG. 9), and cellular uptake efficiency was enhanced by the target-specific peptide introduced on the surface of the recombinant protein (see FIG. 10), leading to cytosolic release and silencing of target gene (see FIGS. 11 to 13).

Due to the RGD peptide, the recombinant protein of the present invention shows a target-specificity to cancer cells in animal cancer models (FIG. 14), and delivers siRNA into the cancer tissues of animal cancer models to induce silencing (see FIGS. 15 to 18), thereby being used as a siRNA delivery carrier.

In still another embodiment, the present invention relates to a composition for siRNA delivery, comprising the recombinant protein and siRNA, wherein the siRNA binds to a siRNA binding protein to be located in the interior cavity of the recombinant protein.

Further, the present invention relates to a method for delivering siRNA, comprising the step of administering the recombinant protein and siRNA to a subject, wherein the siRNA binds to a siRNA binding protein to be located in the interior cavity of the recombinant protein.

In the present invention, siRNA is characterized in that it binds to the siRNA binding protein constituting the recombinant protein of the present invention, and thus is encapsulated within the recombinant protein particle. The siRNA encapsulated within the recombinant protein particle is blocked from the outside to be protected from nucleases, thereby showing excellent stability. The cellular uptake of siRNA is effectively mediated by target-specific peptide exposed on the recombinant protein particle, and thus siRNA can be internalized via endocytosis pathways. After cellular uptake, the siRNA bound with the siRNA binding protein is dissociated from the siRNA binding protein under acidic condition of the endosome in the cell, leading to endosomal escape. Consequently, mRNA expression can be effectively suppressed. Thus, disease therapy can be achieved by suppressing the expression of target genes including disease genes.

Preferably, if the RGD (Arg-Gly-Asp) peptide is bound on the surface of the recombinant protein, siRNA can be effectively delivered into cancer cell or tissues.

In still another embodiment, the present invention relates to a composition for the treatment of diseases associated with siRNA, comprising the recombinant protein for siRNA delivery and siRNA, wherein the siRNA binds to a siRNA binding protein to be located in the interior cavity of the recombinant protein.

Further, the present invention relates to a method for treating diseases associated with siRNA, comprising the step of administering the recombinant protein and siRNA to a subject, wherein the siRNA binds to a siRNA binding protein to be located in the interior cavity of the recombinant protein.

Any siRNA may be used without limitation, as long as it is able to suppress mRNA expression of a disease gene to induce a therapeutic effect, and the siRNA preferably includes those consisting of 20 to 30 nucleotides.

The diseases associated with siRNA may include diseases known to be treated using siRNA, and may be preferably selected from the group consisting of cancer, age-related macular degeneration, viral infections, autoimmune diseases and neurodegenerative diseases, but are not limited thereto. The cancer includes breast cancer, lung cancer, head and neck cancer, brain cancer, abdominal cancer, colon cancer, esophageal cancer, gastric cancer, liver cancer, tongue cancer, neuroblastoma, osteosarcoma, ovarian cancer, pancreatic cancer, prostate cancer, wilm's tumor, retinoblastoma, multiple myeloma, skin cancer, lymphoma, and hematologic cancer, but is not limited thereto.

Preferably, if the RGD (Arg-Gly-Asp) peptide is bound on the surface of the recombinant protein, siRNA can be effectively delivered into cancer cell or tissues, thereby being used for the treatment of cancer.

An effective dose of the recombinant protein may be suitably determined depending on the type and purpose, the patient's condition, etc. Further, the therapeutic composition may be administered to mammals including human via various routes. All possible routes of administration may be expected, including oral, rectal, intravenous, intramuscular, subcutaneous, intrauterine or intracerebroventricular routes. The pharmaceutical composition of the present invention may be formulated into oral preparations such as a powder, a granule, a tablet, a capsule, a suspension, an emulsion, a syrup, and an aerosol, or parenteral preparations such as a transdermal preparation, a suppository and a sterile injectable solution, according to the common methods.

Hereinafter, the present invention will be described in detail with reference to Examples. However, the following Examples are for illustrative purposes only, and the invention is not intended to be limited by the following Examples.

Example 1

Preparation of Recombinant Protein for siRNA Delivery 1-1. Design of Recombinant Protein of the Present Invention The present inventors designed a recombinant protein for siRNA delivery, which forms a spherical particle, and they performed the 3D structural simulation.

First, the amino acid sequence of FIG. 1 was determined as a subunit constituting the recombinant protein of the present invention. As shown in FIG. 1, RGD peptide (SEQ ID NO. 3: CDCRGDCFC) was replaced at positions Ala80 and Ser81 in the amino acid sequence (1-149) prepared by removing the C-terminus from the total 185 amino acids constituting the subunit of HBV capsid protein (SEQ ID NO. 1 or GenBank CAA26537.1). In addition, a capsid protein and a p19 protein were linked with each other using 31 amino acids (SEQ ID NO. 4: GSSGGSGSSGGSGGGDEADGSRGSQKAGVDE) as a linker. The p19 protein was designed to have the amino acid sequence at 3 to 172 positions of the amino acid sequence constituting the p19 siRNA binding protein (SEQ ID NO. 2 or GenBank CAA59481.1) derived from CIRV (Carnation Italian ringspot virus).

The designed recombinant protein has the three dimensional structure shown in FIG. 2. The recombinant protein of the present invention forms a single spherical particle that contains 240 subunit proteins. In this regard, two subunit proteins forms one dimer cluster, which produces spikes on the surface of the particle, and the RGD peptide is placed on the surface-exposed spike. Thus, 240 RGD peptides are exposed on one particle. In addition, the p19 protein fused at the C-terminus of the capsid protein binds with siRNA, and consequently the siRNA is located in the interior cavity of the recombinant protein particle. Thus, a single recombinant protein particle could accommodate 120 siRNAs.

The present inventors performed the 3D structural simulation using the Pymol program (version 1.4.1, DeLano Scientific LLC) for 3D structural analysis so as to demonstrate that siRNA molecules could freely pass through the holes on the surface of the designed virus particle (FIG. 3). Three dimer clusters form one hole on the surface of the recombinant protein particle, and thus one recombinant protein particle has 40 holes. The hole has a diameter of 1.2 nm or more and the amino acids constituting the hole are flexible, whereas a double stranded siRNA has a diameter of 1 nm. Therefore, siRNA molecules could freely pass through the holes.

1-2. Mass-Production and Purification of Recombinant Protein Using *E. Coli*

In order to prepare the recombinant protein designed in Example 1-1, a gene encoding the HBV capsid protein was first amplified by PCR using a forward primer 5'-ATGGACATTGACCCGTATAAA-3' (SEQ ID NO. 6) and a reverse primer 5'-AACAACAGTAGTTTCCGG-3' (SEQ ID NO. 7), and a gene encoding the p19 protein was amplified by PCR using a forward primer 5'-CGAGCTATACAAGGAAACGAC-3' (SEQ ID NO. 8) and a reverse primer 5'-CTGAGCTCCTCGCTTTCTTTCTTGAAGGT-3' (SEQ ID NO. 9). The PCR amplification was performed for 30 cycles consisting of denaturation at 95° C./30 sec, annealing at 60° C. and elongation at 72° C./2 min. The two amplified PCR products were mixed with a forward primer 5'-ACTACTGTTGTTGGTTCAAGCGGCGGTTCCGGTTCAAGTGGCGGATCCGGAGGCGGTGATGAAGCTGACGGCTCCCGTGGTTCACAAAAAGCTGGTGTCGACGAA-3' (SEQ ID NO. 10) and a reverse primer 5'-TTCGTCGACACCAGCTTTTTGTGAACCACGGGAGCCGTCAGCTTCATCACCGCCTCCGGATCCG CCACTTGAACCGGAACCGCCGCTTGAACCAACAACAGTAGT-3' (SEQ ID NO. 11) which are the primers corresponding to the commercially synthesized linker peptide, and then PCR amplification (30 cycles consisting of denaturation at 95° C./30 sec, annealing at 60° C. and elongation at 72° C./2 min) was performed using the forward primer of the HBV gene and the reverse primer of the p19 gene, thereby obtaining a gene construct which is a linkage of the HBV capsid gene, linker peptide gene, and p19 protein gene.

In order to insert the RGD peptide, the corresponding forward primer 5'-GAAGATCCATGTGACTGCCGCGGTGATTGTTTCTGTAGGGATCTA-3'(SEQ ID NO. 12) and reverse primer 5'-TAGATCCCTACAGAAACAATCACCGCGGCAGTCACATGGATCTTC-3'(SEQ ID NO. 13) were mixed with the recombinant gene, and then PCR amplification (30 cycles consisting of denaturation at 95° C./30 sec, annealing at 60° C. and elongation at 72° C./2 min) was performed using the forward primer of the HBV gene and the reverse primer of the p19 gene, so as to amplify the recombinant gene designed in Example 1-1.

The amplified gene has NdeI and XhoI restriction sites, and thus treated with the restriction enzymes, followed by purification. In the same manner, a pET28a vector (NEB Inc.) was also treated with the same restriction enzymes, and then purified. The recombinant gene was inserted using a DNA ligase, followed by transformation of the competent cells using a Hanahan method. The gene insertion was examined by colony PCR and finally, the sequence was examined by DNA sequencing.

After transformation of BL21 (DE3) host cells (Novagen) with the gene-inserted expression vector, the cells were cultured in an LB medium (Sigma-Aldrich) at 37° C. When $OD_{600}$ reached 0.5, expression was induced using 1 mM IPTG (Isopropyl β-D thiogalactoside). Thereafter, the cells were cultured at 18° C. for 6 hours, and then collected, followed by cell lysis using a lysis buffer (50 mM Tris-HCl, 8.0, 100 mM NaCl, 1 mM PMSF (phenylmethylsulfanylfluoride)). The cell lysate was only purified.

Since the expression vector is characterized by N-terminal histidine-tagged recombinant protein, affinity chromatography and size exclusion chromatography were performed to purify the protein.

The affinity chromatography was performed using a Ni-NTA column (GE healthcare), and a buffer A (50 mM Tris-HCl, 8.0, 100 mM NaCl) was used to prepare the column and to wash the column after protein loading. The proteins bound to column were eluted using a buffer B (50 mM Tris-HCl, 8.0, 100 mM NaCl, 500 mM Immidazole), and electrophoresis (Laemmli, U. K. Nature 1970, 227, 680-685.) was performed to examine the molecular weight. Further, the size exclusion chromatography was performed using Superdex 200 10/300 GL column (GE Heathcare), and the injection volume was 2 mL, and a buffer of 50 mM Tris-HCl (8.0) and 100 mM NaCl was used. After purification, the protein was concentrated to approximately 1 mg/mL, and stored using 50 mM PBS (7.4).

Experimental Example 1

Examination of Spherical Particle Formation and siRNA Binding Affinity of Recombinant Protein of the Present Invention siRNAs were encapsulated within the recombinant protein for siRNA delivery prepared in Example 1-2, and siRNA binding affinity was examined. In this experiment, a RFP (Red Fluorescent Protein)-targeting siRNA was used, and the used siRNA has the following base sequence:

```
Sense strand:
                                      (SEQ ID NO. 14)
5'-UGUAGAUGGACUUGAACUCdTdT-3'

Antisense strand:
                                      (SEQ ID NO. 15)
5'-UGAAGUUGCACUUGAAGUCdTdT-3'
```

In order to examine the siRNA encapsulation, the siRNA was labeled with FITC (fluorescein isothiocyanate), and then bound with the recombinant protein, followed by size exclusion chromatography. The size exclusion chromatography was performed using Superdex 200 10/300 GL column (GE Heathcare), and the injection volume was 2 mL, and a buffer of 50 mM Tris-HCl (8.0) and 100 mM NaCl was used.

As a result, FIG. 4 shows that the recombinant protein formed a particle by self-assembly. When the peak fractions of spherical particle formation were analyzed by fluorescence spectrophotometer, FITC emission spectra were not observed in no siRNA-encapsulated recombinant protein particle (control) (FIG. 4, brown line), but the emission spectra were observed at different concentrations of the siRNA-encapsulated recombinant protein particles, indicating encapsulation of siRNA within the recombinant protein particle.

Further, in order to determine a molar ratio of siRNA to the recombinant protein particle, the amount of the complexed siRNA was analyzed by electrophoresis, while the recombinant protein particle's concentration was increased relative to the fixed amount of free siRNA.

As shown in FIG. 5, as the recombinant protein particle's concentration was increased, the amount of the uncomplexed free siRNA proportionally decreased, resulting in the increased band thickness by a gel shift, which is attributed to binding of siRNAs to the recombinant protein particles. The quantitative analysis showed that 120 siRNA molecules bind with one recombinant protein particle.

As shown in FIG. 6, the electron microscopy images (CM 20 electron microscope, Philips) showed that the recombinant protein prepared according to the present invention formed a spherical particle with a diameter of approximately 36 nm, similar to HBV, and the siRNA/recombinant protein complex also formed a spherical particle with the same diameter.

Experimental Example 2

Test on Cytotoxicity of Recombinant Protein of the Present Invention

Figure 7:
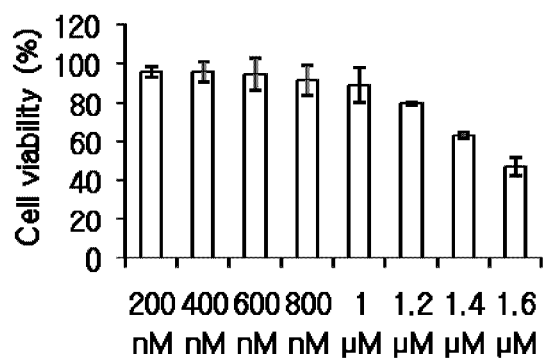
FIG. 7 is the results of MTT assay showing the cytotoxicity and biocompatibility of the recombinant protein particles of the present invention according to their concentrations.

In order to examine cellular biocompatibility of the recombinant protein of the present invention, a MTT assay was performed. Specifically, HeLa cells in an exponential growth phase were cultured in a 96-well plate at a density of 20000 cells/well, and then each well was treated with various concentrations of the recombinant protein particle, followed by cultivation for 24 hours. 200 uL of MTT solution (0.5 mg/mL) was added to each well and reacted for 4 hours. Then, 200 uL of DMSO was added and reacted for 10 minutes. The quantity was measured at 570 nm by ELISA, and the results are shown in FIG. 7. More specific procedures are described in reference (Choi, Y. H.; Liu, F.; Kim, J. S.; Choi, Y. K.; Park, J. S.; Kim, S. W. J. Control. Rel. 1998, 54, 39-48).

As shown in FIG. 7, the recombinant protein particle of the present invention showed a biocompatibility up to 1 μM, and the preferred concentration of the recombinant protein particle of the present invention could be determined as 800 nM.

Experimental Example 3 pH-Dependent siRNA Binding Affinity of Recombinant Protein of the Present Invention The siRNA delivery carrier is inspired by the endosomal escape mechanism under acidic condition of the endosome for cytosolic release after cellular uptake by endocytosis. Thus, in order to determine the pH-dependent siRNA binding affinity of the recombinant protein of the present invention, a PBS buffer was used for pH 7.4 condition, and a 50 mM sodium acetic acid buffer for pH 6.5-5.0 conditions. The recombinant protein particle/siRNA complex was left at room temperature for 10 minutes at each pH condition, and then electrophoresis (200 V, 100 mA) was performed to analyze the binding affinity. For convenient analysis, FITC-labeled siRNAs were used.

Figure 8:
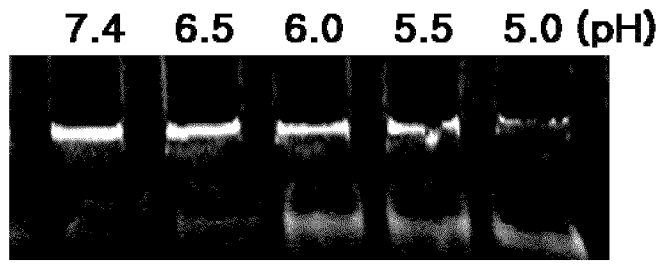
FIG. 8 is the results of electrophoresis showing that siRNAs are dissociated from the recombinant protein particle by pH drop.

As shown in FIG. 8, the recombinant protein particle of the present invention showed excellent siRNA binding affinity at neutral pH. However, the siRNAs began to be dissociated at approximately pH 6.5, and most of the siRNAs were dissociated at approximately pH 5.5. These results indicate that the recombinant protein particle of the present invention is able to deliver siRNA into the cytosol by endosomal escape after cellular uptake.

Experimental Example 4

In Vivo Stability of siRNA Encapsulated in Recombinant Protein Particle of the Present Invention The siRNAs encapsulated within the recombinant protein particle of the present invention are physically protected by the capsid protein from the environment, thereby having excellent resistance to ribonucleases, compared to naked siRNAs. In order to examine this fact, naked siRNAs and siRNAs encapsulated in the recombinant protein particle were left at room temperature under 10% FBS (fatal bovine serum) containing various ribonucleases capable of degrading siRNAs for different time periods, and electrophoresis was performed to compare their degradation.

Figure 9:
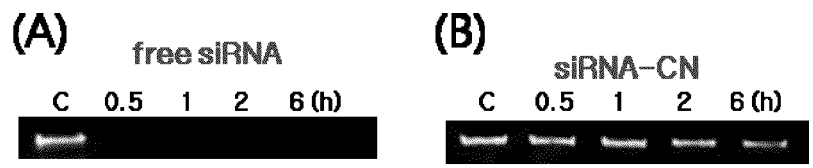
FIG. 9 is the results of stability comparison between the naked siRNA and the siRNA bound with the recombinant protein particle under 10% FBS (fatal bovine serum) condition (siRNA+CN: injection of siRNA to recombinant protein particle)

As shown in FIG. 9, the naked siRNAs were fully degraded within 30 minutes, but the siRNAs encapsulated within the recombinant protein particle of the present invention showed stability even after 6 hours, indicating that the recombinant protein particle of the present invention is an excellent delivery carrier to remarkably enhance in vivo stability of siRNAs.

Experimental Example 5

Cellular Uptake Efficiency of Recombinant Protein Particle of the Present Invention In order to examine the selective cellular uptake of the recombinant protein particle of the present invention, a murine melanoma cell line B16F10 was used to perform a cellular uptake experiment.

Specifically, for convenient fluorescence microscopy, fluorescence Cy5.5 was first conjugated to lysine residues on the exterior surface of the recombinant protein particles. The B16F10 cells were treated with 0.25 µM of the recombinant protein particles, and then observed under a fluorescence microscope at 10 min interval. An Axioskop2 FS plus imaging microscope (ZEISS) equipped with Achroplan IR40 x/0.80W lens, Axiocam black and white CCD camera (Carl Zeiss) was used as a fluorescence microscope.

As shown in FIG. 10, the cellular uptake was observed at 10 minutes after treatment with the recombinant protein particle of the present invention, and the maximum cellular uptake was observed at approximately 30 minutes, indicating very excellent cellular uptake efficiency of the nanoparticle of the present invention.

In order to examine whether this excellent cellular uptake efficiency is attributed to endocytosis by RGD peptides exposed on the surface of the recombinant protein particle, the cells were preincubated with a 100-, 200-, or 400-fold molar excess of RGD peptide (CDCRGDCFC amino acid sequence) (Seq Id NO: 3), and then treated with the recombinant protein particles.

As shown in FIG. 10A, the cellular uptake was remarkably reduced, indicating that cellular uptake is attributed to the RGD peptides exposed on the surface of the recombinant protein particle. As shown in FIG. 10B, preincubation with a 100-, 200-, or 400-fold molar excess of RGD peptide showed 40%, 95%, or 95% reductions, upon comparison of the cellular uptake of the recombinant protein particle without the RGD peptide.

Experimental Example 6

Intracellular Delivery of siRNA and Gene Silencing by Recombinant Protein Particle of the Present Invention 6-1. Fluorescence Image Analysis The gene silencing efficacy of siRNAs delivered by the recombinant protein particle of the present invention was compared to that of the known siRNA delivery carrier, Lipofectamine. The equal amounts of siRNAs were mixed with Lipofectamine and the recombinant protein particle of the present invention, and treated to the RFP-expressing B16F10 melanoma cells. After 24 hours, fluorescence microscopy was performed.

Figure 11:
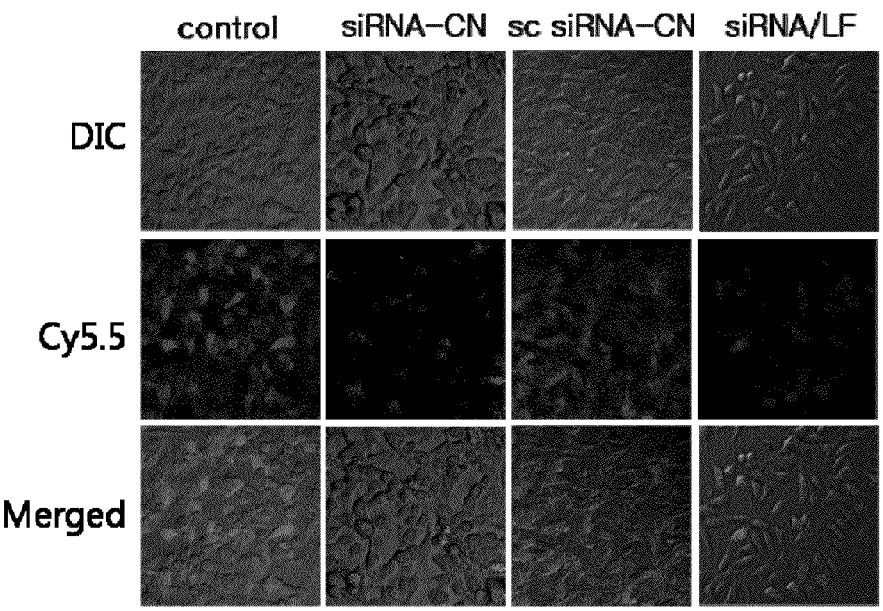
FIG. 11 is the results of fluorescence microscopy showing the RFP gene silencing in the cells by siRNAs encapsulated in the recombinant protein particle (Control: RFG-expressing B16F10 cell, siRNA-CN: injection of siRNAs into cells using the recombinant protein particle, sc siRNA-CN: injection of mismatched scrambled RFP siRNAs encapsulated in the recombinant protein particle into cells, siRNA/LF: use of the known siRNA delivery carrier, Lipofectamine)

As shown in FIG. 11, strong fluorescence intensity was observed in the non siRNA-treated control cells expressing RFP fluorescent protein, but RFP expression was suppressed in the cells treated with a complex of siRNA and Lipofectamine or with a complex of siRNA and the recombinant protein particle.

Figure 12:
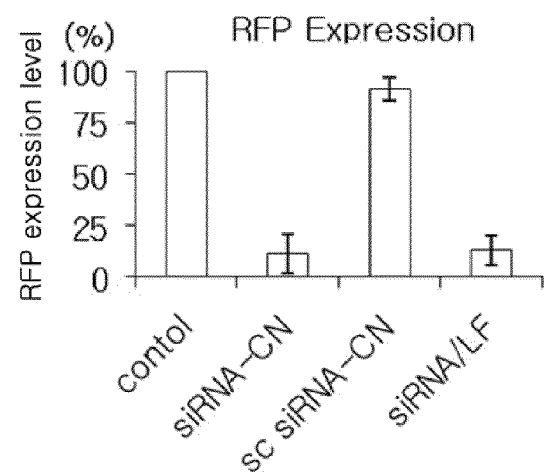
FIG. 12 is the results of quantifying fluorescence intensities of the expressed RFP shown in FIG. 11 (Control: RFG-expressing B16F10 cell, siRNA-CN: injection of siRNAs into cells using the recombinant protein particle, sc siRNA-CN: injection of mismatched scrambled RFP siRNA encapsulated in the recombinant protein particle into cells, siRNA/LF: use of the known siRNA delivery carrier, Lipofectamine)

As shown in FIG. 12, the gene silencing was not observed in the cells treated with a complex of a mismatched scrambled RFP siRNA and the recombinant protein particle. In the quantitative analysis of the RFP gene silencing, the complex of siRNA and Lipofectamine and the complex of siRNA and the recombinant protein particle showed approximately 93% and 95% suppression of gene expression, respectively.

6-2. RT-PCR Analysis

The present inventors also performed RT-PCR for mRNA quantitative analysis to examine siRNA delivery efficacy of the recombinant protein particle of the present invention. More specifically, a set of primers corresponding to RFP mRNA (forward primer 5'-GGCTGCTTCATCTACAAGGT-3' (SEQ ID NO. 16) and reverse primer 5'-GCGTCCACG-TAGTAGTAGCC-3' (SEQ ID NO. 17)) and a set of primers corresponding to β-actin (forward primer 5'-AGAGG-GAAATCGTGCGTGAC-3' (SEQ ID NO. 18) and reverse primer 5'-CAATAGTGATGACCTGGCCGT-3' (SEQ ID NO. 19)) for the control were used to perform RT-PCR for the RFP mRNA quantification (denaturation at 95° C./30 sec, annealing at 51° C./30 sec, and elongation at 72° C./30 sec, 20 cycles). After electrophoresis, each band was quantified using a DNR's GelQuant (image analysis) program.

As shown in FIG. 13, each of the complex of siRNA and Lipofectamine and the complex of siRNA and the recombinant protein particle showed approximately 85% and 90% reduction, compared to the control group.

Experimental Example 7

Cancer Targeting of Recombinant Protein Particle of the Present Invention in Animal Cancer Model The cancer-specific RGD peptide introduced on the surface of the recombinant protein particle of the present invention was used to examine whether the recombinant protein particle is effectively able to target cancer in a mouse cancer model. The B16F10 melanoma cells were subcutaneously injected into the left flank of mice to prepare a mouse cancer model. The recombinant protein particles with RGD and without RGD were injected into the mouse animal models via tail vein at an amount of 50 µg/mouse, respectively. The mice were observed using a 12-bit CCD camera (Kodak Image Station) for each time. For convenient observation of cancer targeting, a fluorescent dye Cy5.5 (NHS-ester) was conjugated to the lysine residues of each recombinant protein particle.

As shown in FIG. 14, it was observed that the recombinant protein particles with RGD peptides began to accumulate in the cancer tissue 3 hours after injection, and the accumulation reached the maximum about 72 hours after injection. Further, upon prolonging the observation time to 96 hours, accumulation of the recombinant protein particles was still observed in the cancer tissue. However, accumulation of the recombinant protein particles without RGD peptides was not observed in the cancer tissue even after 96 hours. Accumulation of the recombinant protein particle with RGD was also slightly observed in the liver, but accumulation of the recombinant protein particle without RGD was relatively low in the liver. These results indicate that the recombinant protein particles of the present invention are effectively accumulated in the cancer tissues and circulated in vivo for a relatively long period of time owing to the RGD peptides exposed on their surface.

Figure 15:
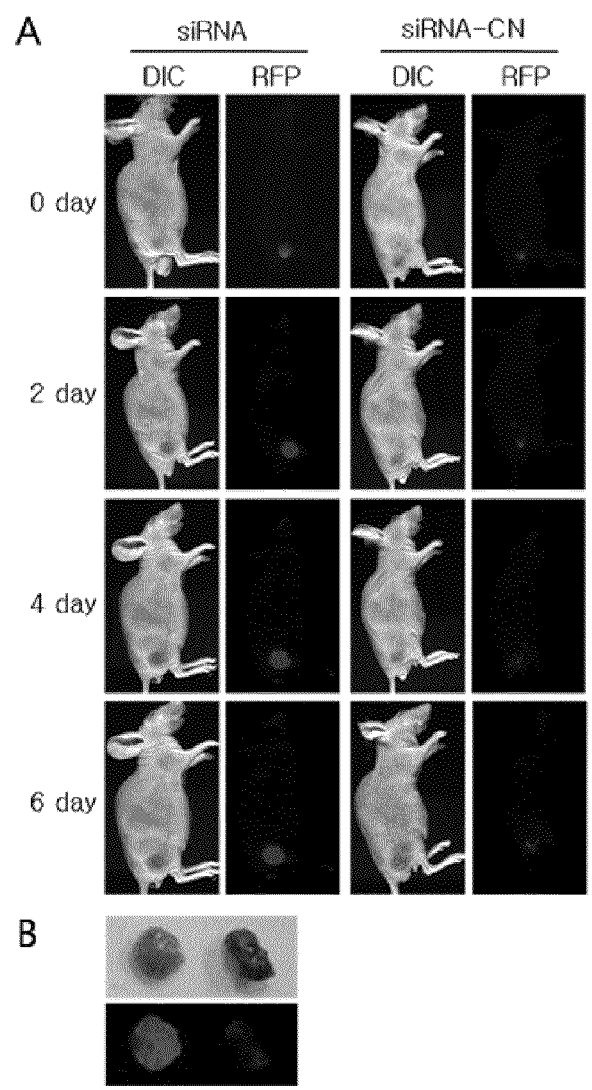
FIG. 15(A) is the results of fluorescence analysis showing the RFP gene silencing in animal cancer models by siRNAs encapsulated in the recombinant protein particle (siRNA: injection of free siRNAs without recombinant protein particles, siRNA-CN: injection of siRNAs into cells using recombinant protein particle)
FIG. 15(B) is the results of fluorescence analysis of the cancer tissue removed 6 days after injection.

Experimental Example 8 siRNA Delivery and Gene Silencing by Recombinant Protein Particle of the Present Invention in Animal Cancer Model 8-1. Fluorescence Image Analysis The gene silencing efficacy of siRNAs delivered by the recombinant protein particle of the present invention was examined in an animal cancer model. For convenient examination of gene silencing efficacy, the RFP-expressing B16F10 melanoma cells were injected into the left flank of mice to prepare a mouse cancer model. When RFP signals were observed in the cancer tissues, siRNAs encapsulated in the recombinant protein particles were injected via tail vein. For comparison, free siRNAs were injected in the same manner without using the delivery carrier. When the cancer with a size of approximately 5-8 mm was observed in the mice, siRNAs encapsulated in the recombinant protein particles (siRNA-CN, 50 µg of siRNA/mouse) were injected via tail vein three times every other day for 6 days. RFP signals were non-invasively observed in the cancer tissue using a 12-bit CCD camera As shown in FIG. 15, an increase in RFP signals was proportional to cancer growth of B16F10 and the gene silencing was not observed in the free siRNA-treated mice. However, when siRNAs were injected using the recombinant protein particle of the present invention as a delivery carrier, RFP signals were remarkably decreased.

Figure 16:
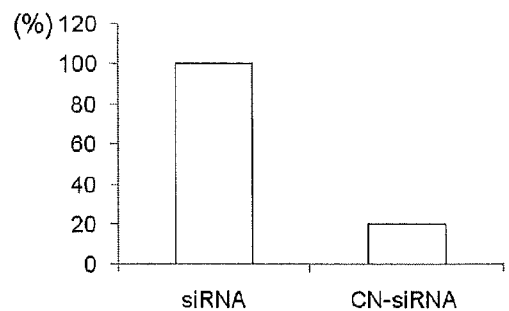
FIG. 16 is the result of quantifying fluorescence intensities of the expressed RFP in FIG. 15 (siRNA: injection of free siRNA without recombinant protein particles, siRNA-CN: injection of siRNA into cells using recombinant protein particle)

As shown in FIG. 16, RFP photon counts per gram of cancer removed at 6 days were reduced by approximately 5-fold, compared to that of free siRNA.

These results indicate that the recombinant protein particle of the present invention showed excellent cancer targeting efficacy and therapeutic effects as a siRNA delivery carrier, compared to free siRNA.

8-2. Immunohistochemical Staining Assay

The present inventors performed an immunohistochemical staining assay using RFP antibodies in the cancer tissues that were removed from the animal cancer model 6 days after injection of the recombinant protein particle, so as to analyze the RFP expression for the examination of siRNA delivery efficiency of the recombinant protein particle of the present invention. Specifically, the cancer tissues were removed from the mice 6 days after injection, and fixed in paraffin, followed by staining using RFP primary antibodies.

Figure 17:
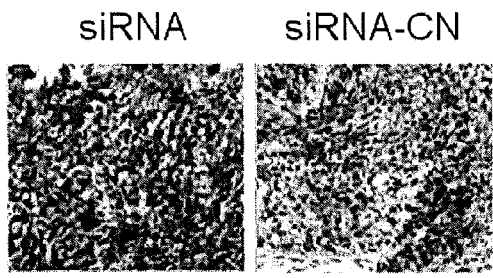
FIG. 17 is the result of immunohistochemical staining assay showing the RFP gene silencing in animal cancer models by siRNAs encapsulated in the recombinant protein particle (siRNA: injection of free siRNA without recombinant protein particles, siRNA-CN: injection of siRNA into cells using recombinant protein particle)

As shown in FIG. 17, high expression of RFP protein was observed in the free siRNA-treated cancer tissues, but a notable reduction in the staining with RFP antibodies was observed in the cancer tissues treated with siRNAs encapsulated in the recombinant protein particle of the present invention. These results demonstrate that the gene silencing was effectively achieved by siRNAs delivered by the recombinant protein particle of the present invention.

8-3. RT-PCR Analysis

The present inventors also performed RT-PCR for mRNA quantitative analysis using the cancer tissues removed from the animal cancer model 6 days after injection of the recombinant protein particle, so as to examine siRNA delivery efficacy of the recombinant protein particle of the present invention. RNAs were extracted using an RNeasy plus mini kit (Qiagen) from the cancer tissues removed from the mice 6 days after injection, and then RT-PCR (denaturation at 95° C./30 sec, annealing at 60° C./30 sec, and elongation at 72° C./30 sec, 20 cycles) was performed using the primers used in Example 6-2, followed by agarose gel electrophoresis.

Figure 18A:
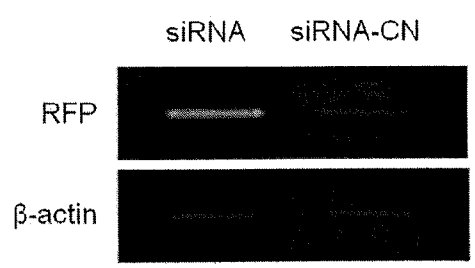
FIG. 18(A) and FIG. 18(B) are the results of RT-PCR and quantitative analysis showing that the RFP mRNA reduction in the cancer tissue removed from the animal cancer model 6 days after injection is caused by siRNAs encapsulated in the recombinant protein particle (siRNA: injection of free siRNA without recombinant protein particles, siRNA-CN: injection of siRNA into cells using recombinant protein particle), respectively.
Figure 18B:
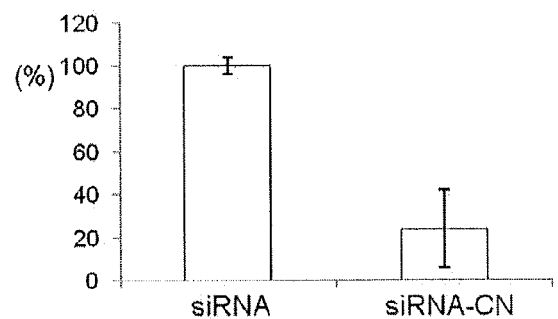

As shown in FIG. 18, approximately 75% RFP mRNA reduction was observed in the cancer tissues treated with siRNAs encapsulated in the recombinant protein particle of the present invention, compared to the free siRNA-treated cancer tissue.

Taken together, it can be seen that the recombinant protein particles of the present invention effectively deliver siRNAs into cancer tissues so as to induce gene silencing.

EFFECT OF THE INVENTION

The recombinant protein of the present invention or the recombinant virus particle formed by the recombinant protein is able to selectively deliver siRNAs into cells or tissues and also greatly enhance in vivo stability, thereby being effectively used as an siRNA therapeutic agent, a composition for cell-based drug screening, and a siRNA delivery carrier for research.

What is claimed is:

1. A recombinant protein delivering siRNA into the cell, wherein the recombinant protein is formed in a spherical particle via a self-assembly of the subunit proteins where a RGD (Arg-Gly-Asp) peptide is located on the exterior surface of the spherical particle and a Carnation Italian ringspot virus (CIRV)-derived p19 protein is located in the interior cavity of the spherical particle, and wherein the subunit protein is a fusion protein comprising the following peptide:

A-B-C where A is a capsid protein of HBV (Hepatitis B virus) that comprises the residues 1-149 of SEQ ID NO: 1 and the RGD (Arg-Gly-Asp) peptide insertion between the residues 80 and 81 of SEQ ID NO: 1;

B is a linker peptide that comprises an amino acid sequence of SEQ ID NO: 4; and C is the CIRV-derived p19 protein that comprises the residues 3-172 of SEQ ID NO: 2 and capable of binding to siRNA.

2. The recombinant protein according to claim 1, wherein the subunit protein consists of an amino acid sequence of SEQ ID NO: 5.

3. A composition for siRNA delivery comprising the recombinant protein of claim 1 and siRNA, wherein the siRNA binds to a siRNA binding protein to be located in the interior cavity of the recombinant protein.

4. The composition according to claim 3, wherein a RGD (Arg-Gly-Asp) peptide is bound on the surface of the recombinant protein to deliver siRNAs into the cancer tissue.

5. A composition for the treatment of diseases associated with siRNA selected from the group consisting of cancer, age-related macular degeneration, viral infections, autoimmune diseases and neurodegenerative diseases, comprising the recombinant protein of claim 1 and siRNA, wherein the siRNA binds to a siRNA binding protein to be located in the interior cavity of the recombinant protein.

6. The composition according to claim 5, wherein a RGD (Arg-Gly-Asp) peptide is bound on the surface of the recombinant protein for the treatment of cancer.

7. A method for delivering siRNA comprising the step of administering the recombinant protein of claim 1 and siRNA to a subject, wherein the siRNA binds to a siRNA binding protein to be located in the interior cavity of the recombinant protein.

8. The method according to claim 7, wherein a RGD (Arg-Gly-Asp) peptide is bound on the surface of the recombinant protein for delivery of siRNAs into cancer tissue.

9. A method for treating diseases associated with siRNA selected from the group consisting of cancer, age-related macular degeneration, viral infections, autoimmune diseases and neurodegenerative diseases comprising the step of administering the recombinant protein of claim 1 and siRNA to a subject, wherein the siRNA binds to a siRNA binding protein to be located in the interior cavity of the recombinant protein.

10. The method according to claim 9, wherein a RGD (Arg-Gly-Asp) peptide is bound on the surface of the recombinant protein and the disease associated with siRNA is cancer.

* * * * *

SEQUENCE LISTING

```
<160> NUMBER OF SEQ ID NOS: 19

<210> SEQ ID NO 1
<211> LENGTH: 185
<212> TYPE: PRT
<213> ORGANISM: Artificial Sequence
<220> FEATURE:
<223> OTHER INFORMATION: HBV capsid protein (GenBank CAA26537.1)

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Val Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125
```

```
Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Pro Ser Pro Arg Arg Arg
                165                 170                 175

Arg Ser Gln Ser Arg Glu Ser Gln Cys
            180                 185

<210> SEQ ID NO 2
<211> LENGTH: 172
<212> TYPE: PRT
<213> ORGANISM: Artificial Sequence
<220> FEATURE:
<223> OTHER INFORMATION: p19 protein of Carnation Italian ringspot virus
      (GenBank CAA59481.1)

<400> SEQUENCE: 2

Met Glu Arg Ala Ile Gln Gly Asn Asp Thr Arg Glu Gln Ala Asn Gly
1               5                   10                  15

Glu Arg Trp Asp Gly Gly Ser Gly Gly Ile Thr Ser Pro Phe Lys Leu
            20                  25                  30

Pro Asp Glu Ser Pro Ser Trp Thr Glu Trp Arg Leu Tyr Asn Asp Glu
            35                  40                  45

Thr Asn Ser Asn Gln Asp Asn Pro Leu Gly Phe Lys Glu Ser Trp Gly
50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
            85                  90                  95

Tyr Ala Ala Ser Arg Phe Leu Gly Ala Asn Gln Val Gly Cys Thr Tyr
            100                 105                 110

Ser Ile Arg Phe Arg Gly Val Ser Val Thr Ile Ser Gly Gly Ser Arg
            115                 120                 125

Thr Leu Gln His Leu Cys Glu Met Ala Ile Arg Ser Lys Gln Glu Leu
130                 135                 140

Leu Gln Leu Thr Pro Val Glu Val Glu Ser Asn Val Ser Arg Gly Cys
145                 150                 155                 160

Pro Glu Gly Ile Glu Thr Phe Lys Lys Glu Ser Glu
                165                 170

<210> SEQ ID NO 3
<211> LENGTH: 9
<212> TYPE: PRT
<213> ORGANISM: Artificial Sequence
<220> FEATURE:
<223> OTHER INFORMATION: RGD peptide

<400> SEQUENCE: 3

Cys Asp Cys Arg Gly Asp Cys Phe Cys
1               5

<210> SEQ ID NO 4
<211> LENGTH: 31
<212> TYPE: PRT
<213> ORGANISM: Artificial Sequence
<220> FEATURE:
<223> OTHER INFORMATION: Linker peptide

<400> SEQUENCE: 4
```

-continued

Gly Ser Ser Gly Gly Ser Gly Ser Ser Gly Gly Ser Gly Gly Asp
1               5                   10                  15

Glu Ala Asp Gly Ser Arg Gly Ser Gln Lys Ala Gly Val Asp Glu
            20                  25                  30

<210> SEQ ID NO 5
<211> LENGTH: 357
<212> TYPE: PRT
<213> ORGANISM: Artificial Sequence
<220> FEATURE:
<223> OTHER INFORMATION: Figure 1

<400> SEQUENCE: 5

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Cys
65                  70                  75                  80

Asp Cys Arg Gly Asp Cys Phe Cys Arg Asp Leu Val Val Asn Tyr Val
                85                  90                  95

Asn Thr Asn Met Gly Leu Lys Ile Arg Gln Leu Leu Trp Phe His Ile
            100                 105                 110

Ser Cys Leu Thr Phe Gly Arg Glu Thr Val Leu Glu Tyr Leu Val Ser
        115                 120                 125

Phe Gly Val Trp Ile Arg Thr Pro Pro Ala Tyr Arg Pro Pro Asn Ala
    130                 135                 140

Pro Ile Leu Ser Thr Leu Pro Glu Thr Thr Val Val Gly Ser Ser Gly
145                 150                 155                 160

Gly Ser Gly Ser Ser Gly Gly Ser Gly Gly Gly Asp Glu Ala Asp Gly
                165                 170                 175

Ser Arg Gly Ser Gln Lys Ala Gly Val Asp Glu Arg Ala Ile Gln Gly
            180                 185                 190

Asn Asp Thr Arg Glu Gln Ala Asn Gly Glu Arg Trp Asp Gly Gly Ser
        195                 200                 205

Gly Gly Ile Thr Ser Pro Phe Lys Leu Pro Asp Glu Ser Pro Ser Trp
    210                 215                 220

Thr Glu Trp Arg Leu Tyr Asn Asp Glu Thr Asn Ser Asn Gln Asp Asn
225                 230                 235                 240

Pro Leu Gly Phe Lys Glu Ser Trp Gly Phe Gly Lys Val Val Phe Lys
                245                 250                 255

Arg Tyr Leu Arg Tyr Asp Arg Thr Glu Ala Ser Leu His Arg Val Leu
            260                 265                 270

Gly Ser Trp Thr Gly Asp Ser Val Asn Tyr Ala Ala Ser Arg Phe Leu
        275                 280                 285

Gly Ala Asn Gln Val Gly Cys Thr Tyr Ser Ile Arg Phe Arg Gly Val
    290                 295                 300

Ser Val Thr Ile Ser Gly Gly Ser Arg Thr Leu Gln His Leu Cys Glu
305                 310                 315                 320

Met Ala Ile Arg Ser Lys Gln Glu Leu Leu Gln Leu Thr Pro Val Glu
                325                 330                 335

```
Val Glu Ser Asn Val Ser Arg Gly Cys Pro Glu Gly Ile Glu Thr Phe
        340                 345                 350

Lys Lys Glu Ser Glu
        355

<210> SEQ ID NO 6
<211> LENGTH: 21
<212> TYPE: DNA
<213> ORGANISM: Artificial Sequence
<220> FEATURE:
<223> OTHER INFORMATION: Forward primer for HBV capsid protein

<400> SEQUENCE: 6
atggacattg acccgtataa a                                              21

<210> SEQ ID NO 7
<211> LENGTH: 18
<212> TYPE: DNA
<213> ORGANISM: Artificial Sequence
<220> FEATURE:
<223> OTHER INFORMATION: Reverse primer for HBV capsid protein

<400> SEQUENCE: 7
aacaacagta gtttccgg                                                  18

<210> SEQ ID NO 8
<211> LENGTH: 21
<212> TYPE: DNA
<213> ORGANISM: Artificial Sequence
<220> FEATURE:
<223> OTHER INFORMATION: Forward primer for p19 protein

<400> SEQUENCE: 8
cgagctatac aaggaaacga c                                              21

<210> SEQ ID NO 9
<211> LENGTH: 29
<212> TYPE: DNA
<213> ORGANISM: Artificial Sequence
<220> FEATURE:
<223> OTHER INFORMATION: Reverse primer for p19 protein

<400> SEQUENCE: 9
ctgagctcct cgctttcttt cttgaaggt                                      29

<210> SEQ ID NO 10
<211> LENGTH: 105
<212> TYPE: DNA
<213> ORGANISM: Artificial Sequence
<220> FEATURE:
<223> OTHER INFORMATION: Forward primer for linker peptide

<400> SEQUENCE: 10
actactgttg ttggttcaag cggcggttcc ggttcaagtg gcggatccgg aggcggtgat    60
gaagctgacg gctcccgtgg ttcacaaaaa gctggtgtcg acgaa                   105

<210> SEQ ID NO 11
<211> LENGTH: 105
<212> TYPE: DNA
<213> ORGANISM: Artificial Sequence
<220> FEATURE:
<223> OTHER INFORMATION: Reverse primer for linker peptide

<400> SEQUENCE: 11
ttcgtcgaca ccagcttttt gtgaaccacg ggagccgtca gcttcatcac cgcctccgga    60
```
tccgccactt gaaccggaac cgccgcttga accaacaaca gtagt                    105

<210> SEQ ID NO 12
<211> LENGTH: 45
<212> TYPE: DNA
<213> ORGANISM: Artificial Sequence
<220> FEATURE:
<223> OTHER INFORMATION: Forward primer for RGD peptide

<400> SEQUENCE: 12
gaagatccat gtgactgccg cggtgattgt ttctgtaggg atcta                    45

<210> SEQ ID NO 13
<211> LENGTH: 45
<212> TYPE: DNA
<213> ORGANISM: Artificial Sequence
<220> FEATURE:
<223> OTHER INFORMATION: Reverse primer for RGD peptide

<400> SEQUENCE: 13
tagatcccta cagaaacaat caccgcggca gtcacatgga tcttc                    45

<210> SEQ ID NO 14
<211> LENGTH: 19
<212> TYPE: RNA
<213> ORGANISM: Artificial Sequence
<220> FEATURE:
<223> OTHER INFORMATION: sense strand of siRNA

<400> SEQUENCE: 14
uguagaugga cuugaacuc                                                 19

<210> SEQ ID NO 15
<211> LENGTH: 19
<212> TYPE: RNA
<213> ORGANISM: Artificial Sequence
<220> FEATURE:
<223> OTHER INFORMATION: antisense strand of siRNA

<400> SEQUENCE: 15
ugaaguugca cuugaaguc                                                 19

<210> SEQ ID NO 16
<211> LENGTH: 20
<212> TYPE: DNA
<213> ORGANISM: Artificial Sequence
<220> FEATURE:
<223> OTHER INFORMATION: Forward primer for RFP

<400> SEQUENCE: 16
ggctgcttca tctacaaggt                                                20

<210> SEQ ID NO 17
<211> LENGTH: 20
<212> TYPE: DNA
<213> ORGANISM: Artificial Sequence
<220> FEATURE:
<223> OTHER INFORMATION: Reverse primer for RFP

<400> SEQUENCE: 17
gcgtccacgt agtagtagcc                                                20

<210> SEQ ID NO 18
<211> LENGTH: 20
<212> TYPE: DNA

-continued

```
<213> ORGANISM: Artificial Sequence
<220> FEATURE:
<223> OTHER INFORMATION: Forward primer for beta-actin

<400> SEQUENCE: 18
agagggaaat cgtgcgtgac                                          20

<210> SEQ ID NO 19
<211> LENGTH: 21
<212> TYPE: DNA
<213> ORGANISM: Artificial Sequence
<220> FEATURE:
<223> OTHER INFORMATION: Reverse primer for beta-actin

<400> SEQUENCE: 19
caatagtgat gacctggccg t                                        21
```